(12) United States Patent
Frisvad et al.

(10) Patent No.: US 7,304,091 B2
(45) Date of Patent: Dec. 4, 2007

(54) STATIN-LIKE COMPOUNDS

(75) Inventors: Jens Christian Frisvad, Lyngby (DK); Lene Lange, Valby (DK); Kirk Schnorr, Holte (DK); Steen Stender, Copenhagen (DK); Thomas Ostenfeld Larsen, Holte (DK)

(73) Assignee: Myco TeO A/S, Lyngby (DK)

( * ) Notice: Subject to any disclaimer, the term of this patent is extended or adjusted under 35 U.S.C. 154(b) by 131 days.

(21) Appl. No.: 10/497,777

(22) PCT Filed: Dec. 3, 2002

(86) PCT No.: PCT/DK02/00812

§ 371 (c)(1),
(2), (4) Date: Jun. 6, 2004

(87) PCT Pub. No.: WO03/048148

PCT Pub. Date: Jun. 12, 2003

(65) Prior Publication Data
US 2005/0228042 A1 Oct. 13, 2005

(30) Foreign Application Priority Data
Dec. 3, 2001 (DK) .............................. 2001 01794

(51) Int. Cl.
*A61K 31/366* (2006.01)
*C07C 65/01* (2006.01)
*C07D 309/30* (2006.01)
(52) U.S. Cl. ................. 514/460; 549/292; 562/466
(58) Field of Classification Search ........ 549/292; 562/466; 514/460
See application file for complete search history.

(56) References Cited

U.S. PATENT DOCUMENTS 4,255,444 A 3/1981 Oka et al.
4,654,363 A 3/1987 Prugh et al.
6,245,800 B1 6/2001 Arduini et al.

OTHER PUBLICATIONS

Carbonell et al., Biochemistry, (2005), vol. 44(35), pp. 11741-748.*
Auclair et al., Bioorganic & Medicinal Chemistry Letters, vol. 11, pp. 1527-1531, (2001).
Istvan et al., Science, vol. 292, pp. 1160-1164 (May 11, 2001).
Endo et al., Journal of Lipid Research, Vo. 33, pp. 1569-157, (1992).
Motti et al., Ann Ital Med Int, vol. 15, pp. 96-102, (2000).
Mundy et al., Science, vol. 286, pp. 1946-1949, (Dec. 3, 1999).
Kwak et al., Nature Medicine, vol. 8, No. 12, pp. 1399-1402, (Dec. 2000).
Sugiyama et al., Biochemical and Biophysical Research Communications, vol. 271, pp. 688-692, (2000).
Akira Endo et al., Broad-Spectrum Derivatives of Polymyxin B and Colistin, The Journal of Antibiodics, Sep. 11, 1976, pp. 1346-1349, Fermentation Research Laboratories, Sankyo Co., Ltd. 1-2-58 Hiromachi, Shinagawa-ku, Tokyo 140, Japan.
Akira Endo, Monacolin K, A New Hypocholesterolemic Agent Produced By A *Monascus* Species, The Journal of Antibiodics, Apr. 27, 1979, pp. 852-852, Fermentation Laboratory, Tokyo Noko University, Saiwaicho, Fuchu-shi, Tokyo, 183 Japan.

* cited by examiner

*Primary Examiner*—Taofiq Solola
(74) *Attorney, Agent, or Firm*—Sughrue Mion, PLLC

(57) ABSTRACT

The present invention relates to compounds with structures resembling natural statins isolated from *Penicillium* sp. (Formula I); where $R_1$ represents OH, $C_6H_5COO$, $R_6COO$ and $R_6$ represents $C_1$–$C_5$ alkyl; $R_{2-4}$ represents H, $C_1$–$C_5$ alkyl $C_1$–$C_5$ acyl, $R_5$ represents H, $CH_3$; and X represents a compound of (Formula II) or (Formula III)

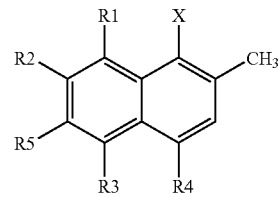

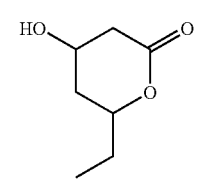

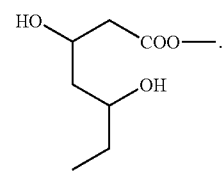

18 Claims, 2 Drawing Sheets

STATIN-LIKE COMPOUNDS

CROSS-REFERENCE TO RELATED APPLICATIONS

This application is a 35 U.S.C. 371 national application of PCT/DK02/00812 filed Dec. 3, 2002, which claims priority or the benefit under 35 U.S.C. 119 of Danish application no. PA 2001 01794 filed Dec. 3, 2001 and U.S. provisional application No. 60/339567 filed Dec. 10, 2001, the contents of which are fully incorporated herein by reference.

FIELD OF INVENTION

The present invention relates to compounds with structures resembling natural statins isolated from *Penicillium* spp. In particular the present invention relates to isolated compounds having UV max relative absorbance spectra as measured by HPLC-DAD, of 222–224 nm (100%), 229–234 nm shoulder (84–89%), 290 nm shoulder (13%), 303–305 nm (14–15%), 318–320 nm shoulder (9–11%), 331–333 nm (7.5–8.5%). Another aspect of the present invention relates to a pharmaceutical composition comprising the compounds of the invention and the use of the compounds as a medicament. Still another aspect of the invention relates to a method for the production of a compound of the inventention. Also an aspect of the invention relates to a method of reducing the level of low-density lipoprotein cholesterol in a human or animal. A further aspect relates to a method of producing a compound of the invention. The isolated compounds can be used in therapy for treatment of hypercholesterolemia or osteoporosis or as precursors for lead compounds with therapeutic effect.

BACKGROUND OF THE INVENTION

The statins comprise natural products (polyketides) from fungi that have a series of strong effects on some of the most important human diseases.

Statins are inhibitors of 3-hydroxy-3-methylglutaryl coenzyme A reductase (HMGR). HMGR is the enzyme responsible for catalyzing the conversion of HMG-CoA to mevalonate, which is an early and rate-limiting step in the cholesterol biosynthetic pathway. Statins are effective lipid lowering agents and thus have been widely used for lowering serum cholesterol levels in the treatment of hypercholesterolemia reducing the risk of heart attacks. Statins also promote bone formation by affecting the expression of the bone morphogenic protein-2 (BMP-2) and this stimulation can have beneficial effects for the treatment of bone fractures and osteoporosis (Mundy et al., Science(1999) 286: 1946–1949; Sugiyama et al., Biochem Biophys Res Commun (2000) 271:688–92). Recently statins have recently also been recognized as a new type of immunomodulator by acting as direct inhibitors of induction of MHC-II expression by INF-γ and thus as repressors of MHC-II-mediated T-cell activation (Kwark et al., Nature Med., (2001) 6: 1399–1402). Naturally occurring statins have antifungal activity (Auclair et al., Bioorganic and Medicinal Chemistry Letters (2001), 11: 1527–1531). Chemically modified statin molecules vary in their retention time in the body, the area of accumulation in the body and effectiveness per dose among other differences (Motti et al., Ann Ital Med Int, 2000, 15: 96–102).

The naturally occurring statins can be subdivided into mevinolins (=monacolins) and compactins. The mevinolins are produced by *Aspergillus terreus* and *Monascus ruber*, while Endo et al. (Journal Antibiotics, (1976), 29: 1346–1348) reports the production of compactins by *Penicillium citrinum*.

Istvan and Deisenhofer, (Science (2001) 292: 1160–1164) have recently disclosed the presumed mechanism of inhibition of the HMGR by natural and chemically synthesized statins.

Due to pleiotropic effects of statins, their reported side effects (gastrointestinal disorders, skin rashes and headache (U.S. Pat. No. 6,245,800)), and the variation in retention time in the body, and effectiveness per dose, a need still exists for statin molecules with unique and desirable properties such as increased effectiveness, less toxicity, altered retention time or concentration in a particular organ compared to commercially available statins.

SUMMARY OF THE INVENTION

In a first aspect the present invention relates to isolated compounds having UV max relative absorbance spectra as measured by HPLC-DAD, of 222–224 nm (100%), 229–234 nm shoulder (84–89%), 290 nm shoulder (13%), 303–305 nm (14–15%), 318–320 nm should (9–11%), 331–333 nm (7.5–8.5%), and UV min relative absorbance spectra as measured by HPLC-DAD at 202–204 nm (26–45%), 254–258 nm (2–3%), 326–328 nm (6–8%).

In a second aspect the present invention relates to a compound of formula (IV),

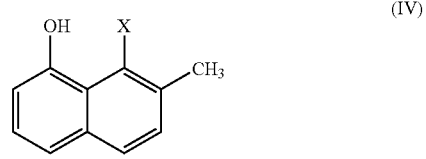

where X represents a compound of formula (II) or (III),

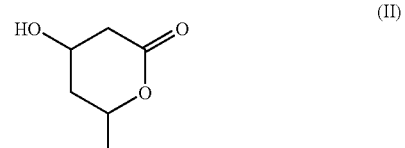

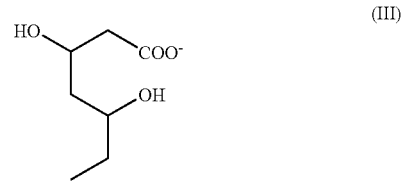

In a third aspect the present invention relates to a pharmaceutical composition comprising at least one of the compounds(s) according to the invention or solistatin or a pharmaceutically acceptable salt or metabolite or prodrug thereof, and a pharmaceutical acceptable carrier.

In a fourth aspect the present invention relates to a use of the compound(s) according to the invention or solistatin for the production of a medicament.

In a fifth aspect the present invention relates to a use of the compound(s) of the invention or solistatin as a medicament.

In a sixth aspect the present invention relates to a use of the compound(s) of the invention for the manufacture of a medicament for the treatment of hypercholesterolemia and/or osteoporosis, or for use as an immunosuppessor.

In a seventh aspect the present invention relates to a method of reducing the level of low-density lipoprotein cholesterol (LDL-C) in a human or animal by administering an effective amount of at least one compound according to the invention or solistatin. In an eigths aspect the present invention relates to a method of producing a compound of the invention, which method comprises
a) culturing a organism in a suitable culture medium under conditions promoting the production of the said compound(s); and
b) recovering the compound(s) from the organism or culture medium obtained in step (a).

DEFINITIONS

Prior to a discussion of the detailed embodiments of the invention, a definition of specific terms related to the main aspects of the invention is provided.

"Statin": The term "statin" according to the present invention means any inhibitor of 3-hydroxy-3-methylglutaryl coenzyme A reductase (HMGR), wherein a HMG-like moiety (present in all known statins) of the statin competes for binding at the active site of the HMG-reductase, with the HMG-moiety of HMG-CoA.

"Solistatin" is a compound of formula (I), wherein $R_1$ is H; $R_{2-4}$ is H; $R_5$ is H, and X is a compound of formula (II).

"Retention index": The retention index or bracketed retention index is based on a series of alkylphenone standards (acetophenone, propiophenone, butyrophenone, valerophenone, hexanophenone, octanophenone and decanophenone) run before each series of HPLC runs. Acetophenone has the RI value 800 (because there are 8 carbon atoms in the molecule), propiophenone is 900 (9 carbon atoms) etc. Based on the retention time of a compound from an extract, the compound is placed between the two alkylphenones eluting before and after the said compound, and the RI value is calculated by linear interpolation (see formula in Frisvad and Thrane, J. Chromatogr.(1987) 404:195–214).

"HPLC-DAD": High performance liquid chromatography with diode array detection (UV detector). UV absorbance of the compound is measured at different (a spectrum) wavelengths simultaneously.

DETAILED DESCRIPTION OF THE INVENTION

Figure 1:
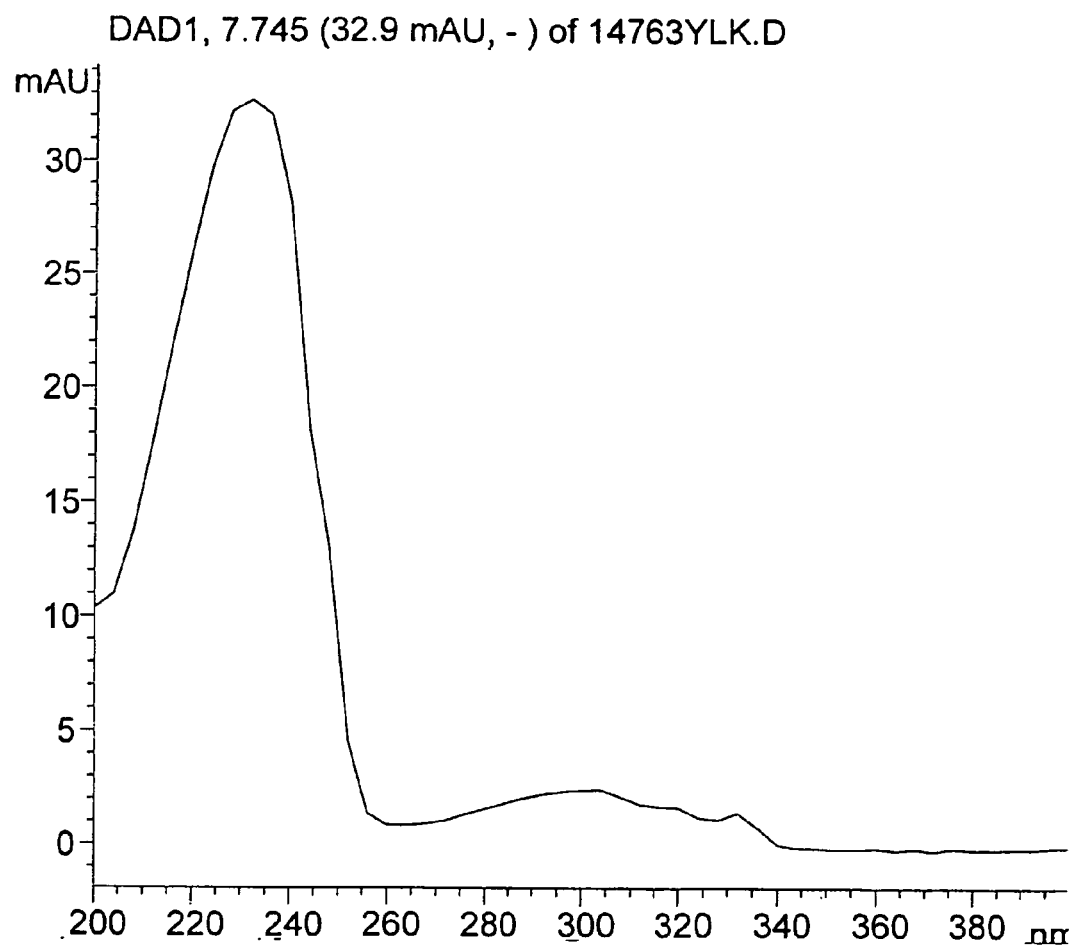
FIG. 1 shows UV-absorbance spectra as measured by HPLC-DAD for the Statans A, $A_1$, and B.

The mevinolins only include one or two double-bonds (the latter a transoid conjugated diene) in the naphthyl part of the molecules giving either uncharacteristic end-absorbtions or the characteristic UV spectrum of the main 1,2,6,7,8,8a-hexahydronaphthyl group (absorbtions at 231, 238 and 247 nm, see FIG. 1 in Endo, J. Antibiotics (1979),32: 852–854). This characteristic chromophore has only been found in the naturally occurring statins and in versiol (LL-N313epsilon). The latter has been found in *Aspergillus versicolor* and *Sporormia affinis* (Turner, Fungal metabolites, Academic Press, London (1971); Turner and Aldridge, Fungal metabolites II, Academic Press, London(1983)). Versiol does not have the delta-lactone (3-hydroxyheptan-5-olide) or its active open acidic form that is important for the activity of the statins (Istvan and Deisenhofer, Science (2001) 292: 1160–1164). For this reason one can screen for statins using high performance liquid chromatography with diode array detection (UV detection) (=HPLC-DAD) (Frisvad and Thrane, J. Chromatogr.(1987) 404:195–214; Frisvad and Thrane, In Betina, V. (Ed.) Chromatography of mycotoxins: techniques and applications J. of Chromatography Library (1993) 54: 253–372) in order to recognize the characteristic chromophore of the 1,2,6,7,8,8a-hexahydronaphthyl group as long as versiol can be excluded. This can be verified by using external standards of mevinolin and compactin in the chromatographic analyses. Mevinolin is always the main statin in the mevinolin secondary metabolite biosynthetic family and compactin is always the main statin in the compactin secondary metabolite biosynthetic family and at least one of them should be present in an extract in order to claim that statins are produced by an organism.

Using the above method fresh isolates of *Penicillium solitum*, were identified as comprising compounds (herein called statans) comprising a chromophore different both from the characteristic chromophore of the 1,2,6,8,8a-hexahydronaphthyl group present in both compactin and mevinolin and the naphthyl group of solistatin as evidenced by UV-spectral data. Said chromophore is different from known secondary metabolites, but has a resemblance to the chromophore of 8-methoxy-1-naphthol (see Stadler, M. et al., Mycological Research 105(10): 1191–1205) and the presence of which is consistently linked to a few compactin producing species. The said chromophore comprised in the compounds of the invention (the statans) and isolated from statin producing isolates of *P. solitum* can be characterized by their unique UV-spectra.

In a first aspect the present invention therefore relates to isolated compounds having UV max relative absorbance spectra as measured by HPLC-DAD, of 222–224 nm (100%), 229–234 nm shoulder (84–89%), 290 nm shoulder (13%), 303–305 nm (14–15%), 318–320 nm shoulder (9–11%), 331–333 nm (7.5–8.5%), and UV min relative absorbance spectra as measured by HPLC-DAD at 202–204 nm (26–45%), 254–258 nm (2–3%), 326–328 nm (6–8%). The isolated compounds characterized by the above UV-spectra (also shown in FIG. 1) are only found in a few compactin producing fungus species, especially of the genus *Penicillium*. The isolated compounds according to the present invention should according to the observed spectra above have structures resembling the naturally occurring statins known as compactin (also known as mevastatin), simvastatin, lovastatin and pravastatin. The compounds could be new members of the statin family or they could be intermediates in the statin metabolic pathway.

In one embodiment of the present invention the isolated compounds comprise statins.

The isolated compounds have similar UV-spectra as defined above, and their alkyl phenone retention index (RI), as defined earlier, is comprised in the range from 887–967 as shown in the example. Furthermore the isolated compounds (statan B, statan A, and statan $A_1$) can be characterized by having a RI selected from the ranges 891–904, 946–959, or 960–964. The compounds according to the present invention are also highly fluorescent when using an excitation wavelength of 230 nm and an emission wavelength of 450 nm.

NMR-Spectrum

As described in the examples, the compound of the invention was purified and NMR-spectra were recorded at 600.13 MHz for $^1$H and 150.92 MHz for $^{13}$C. The chemical shifts are given relative to DMSO (Dimethyl Sulfoxide), 2.5 ppm for $^1$H and 39.5 ppm for $^{13}$C. The NMR-data resulted in a chemical structure of formula (IV) as shown below.

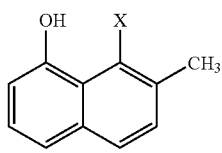

wherein X represents a compound of formula (II) or (III)

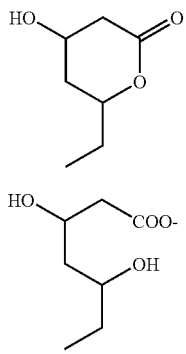

Statan A is the compound of formula (IV) wherein X is the group shown in formula (II).

Statan A may advantageously be used according to the invention as intermediate for preparing other statans of the invention as depicted in formula (I).

In a further aspect the present invention relates to compounds of formula (I)

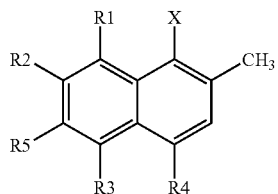

where $R_1$ represents OH, $C_6H_5COO$, $R_6COO$ and $R_6$ represents $C_1$–$C_5$ alkyl;
$R_{2-4}$ represents H, $C_1$–$C_5$ alkyl, or $C_1$–$C_5$ acyl
$R_5$ represents H, $CH_3$; and
X represents a compound of formula (II) or (III)
$R_6$ can be a branched or straight alkyl.

The compounds of formula (I) can be produced from the compound of formula (IV).

Compounds of formula (I) is in context of the present invention referred to as "statans". $R_2$, $R_3$, $R_4$ can be substituted with $C_1$–$C_5$ alkyl or $C_1$–$C_5$ acyl by a Fridel Kraft alkylation or acylation as described in example 8. $R_1$ representing $R_6COO$ where $R_6$ represents $C_1$–$C_5$ alkyl can be produced from a compound of formula (IV) by esterification of the $R_1$ position as described in examples 5 and 6.

In an embodiment $R_1$ is 2-methylbuturyl or 2-dimethylbutyryl or $C_6H_5COO$ (or PhCOO). Benzylation of Statan A at $R_1$ is described in example 7.

Alternatively the esterification may be carried out by a process employing an immobilized lipase enzyme in a nonaqueous system. An example of such a lipase enzyme is *Candida cylindracea C* (Type VII from Sigma Chemical Co.). The process is described in U.S. Pat. No. 5,420,024 and furthermore lists microbes which make the enzyme with the corresponding deposit numbers (see table 1 in U.S. Pat. No. 5,420,024), the content of which is incorporated by reference. Compounds which may be prepared include those wherein R is $R_6$ is ethyl, n-propyl, 2-butyl or 2-methyl-2-butyl.

Statan A can in a further embodiment be used for ether formation, e.g. the formation of statan butyl ether as described in example 9.

$R_5$ can be substituted with methyl using any method know in the art, e.g., as described in TETRAB, Tetrahedron, 44, 18, 1988: 5745–5760 or J. Org. Chem, 48, 17, 1983: 2814–2820 or shown in examples 11 and 12.

Within its scope the invention includes all optical isomers of compounds of the present invention, some of which are optically active, and also their mixtures including racemic mixtures thereof.

Within the scope of the invention are all tautomeric forms of the compounds of the present invention as well as metabolites or prodrugs.

The compounds of the present invention are found in compactin producing species. Accordingly in one embodiment of the present invention the isolated compounds described above are derived from *Penicillium* species, including preferably psychrophilic or psychrotolerant species of *Penicillium*. In another embodiment the said *Penicillium* sp is *P. solitum*. A suitable *P.solitum* strain for providing the compounds of the present invention could in a further embodiment be *P.solitum* CBS 147.86 (deposited at Centraalbureau voor Schimmelcultures). Also the below deposited *Penicillium* species are specifically contemplated, i.e., *P. neocommune*, preferably strain CBS 111,239; *P. novoniwotense*, preferably strain CBS 111,240; *P. landeri*, preferably strain CBS 111,241; *P. lanosum*, preferably strain CBS 111,243; and *P. pinicola*, preferably CBS 111,244.

As discussed above statins have been demonstrated to have several beneficial therapeutic effects as e.g. lipid lowering agents used for lowering serum cholesterol levels, promotion of bone formation for use in osteoporosis, immunosuppressing effects, and new and improved pleiotropic effect.

A further aspect of the present invention therefore relates to a pharmaceutical composition comprising at least one compound according to the invention, or a pharmaceutically acceptable salt or metabolite or prodrug thereof, and a pharmaceutical acceptable carrier.

A "metabolite" of a compound disclosed herein is an active derivative of a compound disclosed herein which is produced when the compound is metabolized. Metabolites of compounds disclosed herein can be identified either by administration of a compound to a host and an analysis of blood samples from the host, or by incubation of compounds with hepatic cells in vitro and analysis of the incubant.

A "prodrug" is a compound that either is converted into a compound disclosed in the application in vivo or has the same active metabolite as a compound disclosed in this application.

Such prodrug form could e.g. be a physiologically-hydrolysable and acceptable ester meaning an ester in which the hydroxyl group is esterified and which is hydrolysable under physiological conditions to yield an acid which is itself physiologically tolerable, at dosages to be administered. The term is thus to be understood as defining regular prodrug forms. Examples of such esters include for example acetates, as well as benzoates of the compounds of the invention.

The salts include pharmaceutically acceptable acid addition salts, pharmaceutically acceptable metal salts or optionally alkylated ammonium salts, such as hydrochloric, hydrobromic, hydroiodic, phosphoric, sulfuric, trifluoroacetic, trichloroacetic, oxalic, maleic, pyruvic, malonic, succinic, citric, tartaric, fumaric, mandelic, benzoic, cinnamic, methanesulfonic, ethane sulfonic, picric and the like, and include acids related to the pharmaceutically acceptable salts listed in Journal of Pharmaceutical Science, 66, 2 (1977) and incorporated herein by reference, or lithium, sodium, potassium, magnesium and the like. Furthermore, the pharmaceutical composition of the invention may comprise at least one compound according to the invention combined with one or more other pharmacologically active compounds.

In another embodiment of the invention the pharmaceutical composition further comprises acetyl salicylic acid.

In a still further embodiment the invention relates to a method for the production of a compound of formula (V) or (I). Formula (V) is formula (I), where $R_1$ represents OH, $R_{2-4}$ represents H, $R_5$ represents $CH_3$, and X represents a compound of formula (II) or (III).

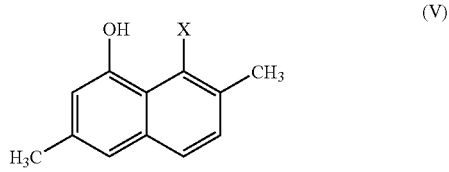

(V)

Compounds of formula (V) may be prepared by methylation of position $R_5$ of the compound of formula (IV) of the invention. Methylation may be carried out using any method known in the art, for instance, as described above or in examples 11 or 12.

Pharmaceutical Compositions

The present invention also relates to pharmaceutical compositions comprising, as an active ingredient, at least one of the compounds of the present invention or a pharmaceutically acceptable salt thereof and, usually, such compositions also contain a pharmaceutically acceptable carrier or diluent.

Pharmaceutical compositions comprising a compound of the present invention may be prepared by conventional techniques, e.g. as described in Remington: The Science and Practise of Pharmacy, 19$^{th}$ Ed., 1995. The compositions may appear in conventional forms, for example capsules, tablets, aerosols, solutions or suspensions.

Typical compositions include a compound of the present invention or a pharmaceutically acceptable acid addition salt thereof, associated with a pharmaceutically acceptable excipient which may be a carrier or a diluent or be diluted by a carrier, or enclosed within a carrier which can be in form of a capsule, sachet, paper or other container. In making the compositions, conventional techniques for the preparation of pharmaceutical compositions may be used. For example, the active compound will usually be mixed with a carrier, or diluted by a carrier, or enclosed within a carrier, which may be in the form of an ampoule, capsule, sachet, paper, or other container. When the carrier serves as a diluent, it may be solid, semi-solid, or liquid material, which acts as a vehicle, excipient, or medium for the active compound. The active compound can be adsorbed on a granular solid container for example in a sachet. Some examples of suitable carriers are water, salt solutions, alcohols, polyethylene glycols, polyhydroxyethoxylated castor oil, syrup, peanut oil, olive oil, gelatine, lactose, terra alba, sucrose, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone.

The formulations may also include wetting agents, emulsifying and suspending agents, preserving agents, sweetening agents or flavouring agents.

The pharmaceutical preparations can be sterilized and mixed, if desired, with auxiliary agents, emulsifiers, salt for influencing osmotic pressure, buffers and/or coloring substances and the like, which do not deleteriously react with the active compounds.

The route of administration may be any route, which effectively transports the active compound to the appropriate or desired site of action, such as oral, nasal, pulmonary, transdermal or parenteral e.g. rectal, depot, subcutaneous, intramuscular or intranasal, the oral route being preferred.

If a solid carrier is used for oral administration, the preparation may be tabletted, placed in a hard gelatin capsule in powder or pellet form or it can be in the form of a troche or lozenge. If a liquid carrier is used, the preparation may be in the form of a syrup, emulsion, soft gelatin capsule or sterile injectable liquid such as an aqueous or non-aqueous liquid suspension or solution.

For nasal administration, the preparation may contain a compound of the present invention dissolved or suspended in a liquid carrier, in particular an aqueous carrier, for aerosol application. The carrier may contain additives such as solubilizing agents, e.g. propylene glycol, surfactants, absorption enhancers such as lecithin (phosphatidylcholine) or cyclodextrin, or preservatives such as parabenes.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

The compounds of the invention may be administered to a mammal, especially a human, in need of such reducing or lowering of the intake of fat food. Such mammals include also animals, both domestic animals, e.g. household pets, and non-domestic animals such as wildlife.

The compounds of the invention may be administered in the form of an alkali metal or earth alkali metal salt thereof, concurrently, simultaneously, or together with a pharmaceutically acceptable carrier or diluent, especially and preferably in the form of a pharmaceutical composition thereof, in an effective amount.

Pharmaceutical compositions containing a compound according to the invention may be administered one or more times per day or week, conveniently administered at mealtimes. An effective amount of such a pharmaceutical composition is the amount that provides a clinically significant effect against consumption of fat food. Such amounts will depend, in part, on the particular condition to be treated, age, weight, and general health of the patient, and other factors evident to those skilled in the art.

The structure of the compounds according to the invention resembles the structure of naturally occurring statins and a further embodiment of the invention thus relates to the use of the said compounds for the production of a statin. The said statin comprises in another embodiment compactin, simvastatin, lovastatin, and pravastatin.

In another embodiment the present invention relates to a use of the compounds of the invention as a medicament. In a still further embodiment the present invention relates to a use of the compounds of the invention for the manufacture of a medicament for the treatment of hypercholesterolemia or osteoporosis or as an immunosuppressor.

A further aspect of the present invention relates to a method of reducing the level of low-density lipoprotein cholesterol (LDL-C) in a human or animal by administering an effective amount of at least one compound according to the invention. In a further embodiment the invention relates to a use of solstatin (Sørensen et al., 1999, Phytochemistry 51:1027–1029) for the preparation of a medicament and in a particular embodiment for the use of the said medicament for treatment of hypercholesterolemia or osteoporosis or as an immunosuppressor.

The compounds of the invention can be produced in any conventional way known to the skilled person by providing a suitable host organism comprising the compound of the invention and growing the said organism in a suitable culture medium under conditions promoting the production of the said compound(s) and recovering the compound(s) from the host organism or culture medium.

It is also contemplated that the culture broth comprising statans after growing the organisms of the invention can be use for the preparation of a pharmaceutical composition.

The said host organism is in one embodiment a fungus.

In another embodiment the said host organism is a *Penicillium* sp. like e.g. a *P. solitum*, including *P. solitum* CBS 147.86 (redeposited as *Penicillium solitum* CBS 111.242 (NN049656) on 29 Nov. 2002) or one of the following deposited strains:

| Deposit | NZ Number | Accession Number | Date of Deposit |
| --- | --- | --- | --- |
| *Penicillium* sp. | NN049653 | CBS 111239 | Nov. 29, 2002 |
| *Penicillium* sp. | NN049654 | CBS 111240 | Nov. 29, 2002 |
| *Penicillium* sp. | NN049655 | CBS 111241 | Nov. 29, 2002 |
| *Penicillium* sp. | NN049657 | CBS 111243 | Nov. 29, 2002 |
| *Penicillium* sp. | NN049658 | CBS 111244 | Nov. 29, 2002 |

The strains have been deposited under conditions that assure that access to the culture will be available during the pendency of this patent application.

These strains were deposited on under the terms of the Budapest Treaty on the International Recognition of the Deposit of Microorganisms for the Purposes of Patent Procedure at Centraalbureau voor Schimmelcultures (CBS), Uppsalalaan 8, 3584 CT Utrecht, The Netherlands.

Strain CBS 111,239 (NN 049653) may be referred to as *Penicillium neocommune* Frisvad (sp.nov) and originates from Wyoming National Forest, US.

Strain CBS 111,240 (NN 049654) may be referred to as *Penicillium novoniwotense* Frisvad (sp.nov) and originates from Faeroe Islands, Denmark.

Strain CBS 111,241 (NN 049655) may be refer to as *Penicillium landeri* Frisvad (sp.nov) and originates from Wind River Range, Wyo., US.

Strain CBS 111,242 (NN049656) is of the species *Penicillium solitum* and has been isolated from apple, Denmark.

Strain CBS 111,243 (NN049657) is of the species *Penicillium lanosum* and has been isolated from soil under spruce tree, Brandy Wine Falls, British Colombia, Canada.

Strain CBS 111,244 (NN049658) may be referred to a *Penicillium pinicola* Frisvad (sp.nov) and originates from Wyom., US.

Statin Activity

Statins are inhibitors of 3-hydroxy-3-methylglutaryl coenzyme A reductase (HMGR). HMGR is the enzyme responsible for catalyzing the conversion of HMG-CoA to mevalonate, which is an early and rate-limiting step in the cholesterol biosynthetic pathway. The compounds of the present invention can be analyzed for their effectiveness as HMGR inhibitors by any method that can directly or indirectly measure the level of LDL-cholesterol in the subject. One such test could be the COBAS INTEGRA® HDL-Cholesterol Direct (Roche Diagnostics). Nielsen et al. (Pharmacology & Toxicology, 1993, 72: 148–151) and Holm et al. (Arteriosclerosis, Thrombosis, and Vascular Biology, 1997, 17: 2264–2272) describes methods for the determination of various forms of cholesterol, both references are hereby incorporated by reference.

In the examples characterization of two distinct compounds is described as well as NMR-spectral analysis for the isolated compound of formula (IV), and animal studies showing the HMGR inhibiting effect of the compounds of the invention.

EXAMPLES

Example 1

Screening for Statans

The fungus *Penicillium solitum* CBS 147.86 (redeposited as CBS 111.242) is inoculated from a resuspension of a preserved freeze-dried spore and inoculated on malt extract agar [according to Blakeslee] (See Samson, R. A., Hoekstra, E. S., Frisvad, J. C. and Filtenborg, O. (eds.) Introduction to food- and airborne fungi. 6th edition., 2000, 378–382) and incubated at 20° C. for 1 week. The conidia are suspended in peptone (0.1%) in water to produce a suspension of approximately 10.000 conidia pr ml. From this suspension 11 cm Petri dishes with 17 ml YES (yeast extract sucrose) agar (Samson, R. A., Hoekstra, E. S., Frisvad, J. C. and Filtenborg, O. (eds.) Introduction to food- and airborne fungi. 6th edition., 2000, 378–382) are 3-point inoculated with a inoculation needle and the YES agar plates incubated at 25° C. for two weeks in the dark. The content of 10 Petri dishes is extracted in a Colworth Stomacher 400 for 2 min with 200 ml ethyl acetate with 1% formic acid. The organic phase is filtered using a hydrophobic filter and the organic solvents evaporated in a rotary evaporator under vacuum at 40° C. The remaining dry extract is re-dissolved in ½ ml methanol, filtered and injected into the HPLC-DAD system (Agilent). The HPLC-DAD system should be connected with an effective fluorescence detector in order to confirm the presence of statans. All compounds should be analyzed using the HPLC-DAD system of Frisvad and Thrane (Frisvad and Thrane, J. Chromatogr.(1987) 404:195–214; Frisvad and Thrane In Betina, V. (Ed.)Chromatography of mocotoxins: techniques and applications J. of Chromatography Library (1993) 54: 253–372) as modified by Smedsgaard (J. Chromatogr. A ,1997, 760: 264–270) with compactin as an external and internal standard and alkylphenones as external standards. In that system the new statin-like compounds (statans) have the following properties:

Statans: Statan A: RI (alkylphenone retention index) average 953 (range 946–959), Statan $A_1$: RI average 961 (range 960–964), statan B: RI average 898 (range 891–904) (as compared to compactin RI average 1108). UV spectra as measured by DAD: (UV max, relative abs.): 222–224 nm (100%), 229–234 nm shoulder (84–89%), 290 nm shoulder (13%), 303–305 nm (14–15%), 318–320 nm shoulder (9–11%), 331–333 nm (7.5–8.5%) (abs. minima at 202–204 nm (26–45%), 254–258 nm (2–3%), 326–328 nm (6–8%)). The statans are highly fluorescing when excitation is performed at 230 nm and using an emission wavelength of 450 nm. Few other secondary metabolites from fungi fluoresce at these conditions (an example is ochratoxin A and B, but these have completely different UV spectra and retention indices).

Example 2

Production and Isolation of Statan A

The isolate CBS 147.86 (redeposited as CBS 111.242) was cultured for 2 weeks in the dark at 20° C. as three point mass inoculations on 1000 Petri dishes (9 cm) on about 20 liter of yeast extract sucrose agar (YES) (yeast extract 20 gr, sucrose 150 g, agar 20 g, distilled water).

The content of the Petri dishes were extracted twice with 10 liter of EtOAC to give ca. 25 g of crude extract which was partitioned between a total of 1 liter of heptane and 1 liter of 90% MeOH in order to remove lipids and apolar compounds. The MeOH fraction was diluted to 60% and extracted with a total of 1 liter of $CH_2Cl_2$ to give a total of 8 g of Statan A (formula IV) rich extract. This extract was then coated onto 8 g of Celite and divided into three portions which subsequently were separated by vacuum liquid chromatography on a $C_{18}$ SPE column (10 g) into four fractions using 100 ml of $H_2O$/MeOH in the following amounts A:(75:25), B:(50:50), C:(25:75) and D:(0:100). The C fraction (4.6 g) rich in Statan A was further separated on a Sephadex LH20 column (25×900 mm) using MeOH at 1 mL/min to give 8 fractions (CA-CF). Finally the CE fraction (96 mg) was subjected to HPLC separation on a Waters Prep Nova-Pak C18 cartridge (25×100 mm, 6 micro m) using $H_2O/CH_3CN$ (65:35) as mobile phase to give 30 mg of pure Statan A.

Example 3

Production of Statans in Submerged Culture

Preparation of Inoculation Material

A petri dish with PDA (potato dextrose agar) was inoculated (at 3-points) with fungal isolate *P. solitum* CBS 147.86 (redeposited as CBS 111.242) and incubated at 25° C. for 7 days.

Conidia were harvested by addition of 5 mL sterile $H_2O$, holding 0.1% Tween per plate. The conidia were released from the mycelium by gentle scraping with pipette tip. The resulting suspension of conidia were poooled from two plates at a time and added to a flask with a total volume of 100 mL $H_2O$ (0.1% Tween, final concentration).

Culture Conditions

A fed batch culture condition in 2 L scale was used.

Composition of medium:
20 g/L yeast extract (Difco),
20 g/L sucrose,
18 mg/L $ZnSO_4.7H_2O$,
8 mg/L $CuSO_4.5H_2O$, 1 ml/L Pluronic (antifoam),
pH ajusted to 5,0 prior to sterilization.

Feed: 500 g/L sucrose, 2 ml/L Pluronic (antifoam).

The fermentation tank was inoculated by adding 2 mL of the spore suspension (described above).

Feed start: 36 h after inoculation, feed rate 2.5 g/L/h.
pH control: >4 (10% NaOH) and <6 (10% $H_3PO_4$).
Temperature: 21° C.
Stirrer speed: start 500 rpm, increased to keep dissolved oxygen >50%, max 1100 rpm.
Airflow: 1 L/min.
Fermentation time 185 h (=8 days).

Extraction of Culture Broth 3 mL of full culture broth was extracted with 3 mL of ethylene acetate (with 1 v/v % formic acid) for 1 hour in ultrasound bath. The ethylene acetate was transferred to a vial and evaporated in a rotary vacuum concentrator. 0.5 mL of methanol was used to redissolve the remains for 1 hour in ultrasound bath. The methanol was filtered though a 0.22 micro m filter into a HPLC-vial.

HPLC conditions: Column: Agilent, Hypersil with BDS-C18, 3 um (mymeter), 4.0×100 mm;
Injection: 10 microL
Flow: 1 mL/min
Gradient: Start at 85% MilliQ $H_2O$ (with 50 ppm TFA) and 15% acetonitrile (with 50 ppm TFA) until 40 min where 100% acetonitrile is reached. 40 to 45 minutes 100% acetonitrile.

Results

The fermentation gave good levels of several statans. Further these fermentation conditions gave a surprisingly low level of other metabolites.

Example 4

Structural Elucidation of Statan A

Accurate mass analysis was done on a Agilent HP 1100 liguid chromatograph with a diode array detector (DAD) coupled to a LCT Micromass oaTOF instrument with Z-spray electro spray source (ESI) and a lockspray probe. 1 microL of sample was injected on an Agilent Hypersil BDS-$C_{18}$ 125×2 mm column with 3 micro m particles. A water-acetonitrile gradient, starting with 15% acetonitrile-water going to 100% acetonitrile in 40 min, maintaining 100% acetonitrile for 5 min, before returning to the start conditions in 8 min equilibrating for 5 min. TFA, 50 ppm was added to the water. The MS was operated in the positive ESI mode using leucineenkephalin as lockmass ([M+H]+ion at 556.2771 Da/e). The molecular ion of protonated Statan A appeared at 301.1421 corresponding to the composition $C_{18}H_{20}O_4$ (Δ–6.3 ppm) corresponding to 9 DBE.

NMR spectra of statans were recorded in 5 mm tubes at 600.13 MHz for $^1H$ and at 150.92 MHz for $^{13}C$ and at 300 K, using DMSO-$d_6$, on a Bruker DRX 600 according to Larsen et al., 2001, (J Agricult and Food Chem 49:

5081–5084). The $^{13}$C and the C,H—COSY spectra revealed the presence of one methyl, four methylene, and two methine groups, together with 5 aromatic protons, two hydroxy protons (9.95 and 5.20 ppm), 5 quaternary aromatic carbon atoms and finally a carboxy group at 170.2 indicating an ester or lactone. The $^1$H and H,H—COSY spectra revealed the presence of one aliphatic (—CH$_2$—CHOH—CH$_2$—CH—CH$_2$—CH$_2$—) and two aromatic spin systems (AB and ABC) together with a single methyl group. Interpretation of the heteronuclear multiple bond coherence spectrum (HMBC) established the structure of Statan A. The chemical shift values of the carbons in the naphthalene part of the molecule were very similar to the values of the model compound 7,8-dimethyl-1-naphtol (Jung, K.-Y., Koreeda, M., 1989, J Organic Chem 54: 5667–5675) and similarly the chemical shift values of the aliphatic part of the molecule were very similar to those reported for solistatin (Sørensen et al., 1999, Phytochemistry 51: 1027–1029) and other statins, altogether strongly supporting the proposed structure.

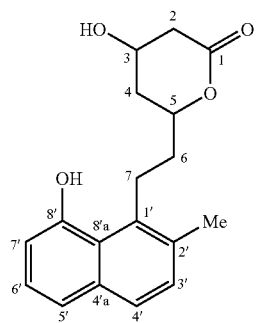

$^1$H NMR (DMSO-d6): δ 9.95 (1H, bs, 8'-OH), 7.54 (1H, d, J=8.2 Hz, H-4'), 7.24 (1H, d, J=8.2 Hz, H-3'), 7.24 (1H, d, J=7.9 Hz, H-5'), 7.16 (1H, dd, J=7.9 and 7.5 Hz, H-6'), 6.83 (1H, d, J=7.5 Hz, H-7'), 5.20 (1H, br s, 3-OH), 4.72 (1H, m, 5-H), 4.16, br s, 3-H), 3.45 (1H, br s, H-7a), 3.36 (1H, br s, H-7b), 2.68 (1H, dd, J=17.2 and 4.7 Hz, H-2a), 2.44 (3H,s, Me), 2.43 (1H, d m, 17.2 Hz, H-2b), 1.92 (2H, m, H-6), 1.91 (1H, m, H-4a), 1.79 (1H, ddd, 14.3, 11.7 and 3.3 Hz, H4b).

$^{13}$C NMR (DMSO-d6): δ 170.2 (C-1), 154.8 (C-8'), 135.1 (C-1'), 135.1 (C-4'a), 132.1 (C-2'), 129.0 (C-3'), 125.8 (C-4'), 124.7 (C-6'), 123.1 (C-8'a), 119.5 (C-5'), 109.9 (C-7'), 75.5 (C-5), 61.0 (C-3), 38.5 (C-2), 36.5 (C-6), 34.8 (C-4), 27.0 (C-7),19.5 (Me).

Example 5

Acetylation of Statan A in Position R$_1$ in Sodium Hydroxide

Synthesis and Recovery of 8-Statanyl Acetate

Dissolve 19 mg of Statan A in 10 percent sodium hydroxide (40 microL) in a glass vial (2 ml). Add crushed ice (about 5 mg) and acetic anhydride (8.2 mg, 7.6 microL) to the vial and shake it for 5 minutes. Subsequently add 200 microL of dichloromethane and shake gently and leave the two phases to separate. Take away the lower layer of dichloromethane and statan acetate and shake it with dilute sodium bicarbonate. Add another 200 microL of dichloromethane to the slightly basic water phase and wash the organic phase with dilute sodium bicarbonate. Take the combined organic phases to dryness. Redissolve the synthesis products in 100 microL of methanol and separate the mixture of mono- an di-acetates by HPLC separation on a Waters Prep Nova-Pak C18 cartridge (25×100 mm, 6 micro m) using H$_2$O/CH$_3$CN (55:45) as mobile phase at a flow rate of 2 mL/min to give 15 mg (66%) of pure 8-acetoxy Statan A and 4 mg of di-acetoxy Statan A.

Example 6

Synthesis and Recovery of 8-Statanyl Isobutyrate

Dissolve 28 mg of Statan A in 1 ml of pyridine in a glass vial (15 mL). Add isobutyric anhydride (25 mg) to the vial and leave it at room temperature for 12 hr. Add crushed ice and leave the reaction mixture for 1 hour. Subsequently add 2 mL of dichloromethane and shake gently and leave the two phases to separate. Take away the lower layer of dichloromethane and Statan A isobutyrate and extract the pyridine-water phase once more with 1 mL of dichloromethane. Wash the combined organic phases first with dilute hydrochloric acid and subsequently with dilute sodium bicarbonate. Take the combined organic phases to dryness. Redissolve the synthesis products in 100 microL of methanol and separate the mixture of 8-statanyl isobutyrate and the di-isobutyrate by HPLC separation on a Waters Prep Nova-Pak C18 cartridge (25×100 mm, 6 micro m) using H$_2$O/CH$_3$CN (55:45) as mobile phase at a flow rate of 2 ml/min to give 24 mg (69%) of pure 8-statanyl isobutyrate.

Example 7

Benzylation of Statan A in Position R$_1$

Synthesis of 8-Statanyl Benzoate

Dissolve 30 mg of Statan A in 10 percent sodium hydroxide (200 microL) in a stoppered glass flask. Add benzoyl chloride (22 mg, 18 µl), close the flask, shake vigorously (15 minutes). Add crushed ice and leave for 5 minutes. Subsequently add 200 microL of dichloromethane and shake gently and leave the two phases to separate. Take away the lower layer of dichloromethane and statanyl benzoate and shake it with dilute sodium bicarbonate. Add another 200 microL of dichloromethane to the water phase and wash the organic phase with dilute sodium bicarbonate. Take the combined organic phases to dryness to give 34 mg (84%) of 8-statanyl benzoate.

Example 8

Acylation of Statan A in Positions R$_2$, R$_3$ and R$_4$

Synthesis and Recovery of 4-, 5- and 7-Acetostatan A by Fries Reaction

Phenolic and naphtolic ketones are produced by the rearrangement of their phenolic or naphtolic esters in the presence of anhydrous aluminium chloride. Mix powdered 8-statanyl acetate (36 mg) and powdered anhydrous aluminium chloride (41 mg) in a small flaks fitted with an air condenser which is closed by a calcium chloride tube. Heat the flask in an oil bath, slowly at first to reach ca. 110° C. in 30 minutes and then at about 160° C. for 1 hour more. Remove the flask from the oil bath, allow to cool, add crushed ice (300 mg) followed by concentrated hydrochloric acid (12 microL) to decompose aluminium salts. Wash the water phase with another 200 microL of dichloromethane. Take the combined organic phases to dryness and redissolve in methanol for separating the reaction mixture by HPLC on a Waters Prep Nova-Pak C18 cartridge (25×100 mm, 6 micro m) using $H_2O/CH_3CN$ (55:45) as mobile phase at a flow rate of 2 mL/min to give pure 4-, 5- and 7-aceto-statan A.

Example 9

Ether formation of Statan A in Position $R_1$

Statan A Butyl Ether—Williamson Synthesis

Weigh out 11.5 mg (0.5 mmol) of clean sodium into a dry flask provided with a double surface condenser, and add 250 microL of ethanol. Add a solution of 150 mg (0.5 mmol) of pure Statan A in 100 microL of absolute ethanol and shake. During shaking for 15 minutes add 133 mg (82.5 microL, 0.72 mmol) of butyl iodide. Boil the solution gently for three hours before distilling off as much as possible of the alcohol. Add water (400 microL) and dichloromethane (200 microL) to the residue in the flask, separate the organic layer and wash it twice with with 200 microL portions of 10 per cent sodium hydroxide solution, then subsequently with water, dilute sulphuric acid and water: dry with magnesium sulphate.

Example 10

Formation of Statan A Carboxylic Acids

Synthesis of 5- and 7-Statan A Carboxylic Acids—Kolbe-Schmidt Reaction

Place a solution containing 109 mg of Statan A, 200 mg of potassium hydrogen carbonate and 5 mL of water in a flask fitted with a reflux condenser and gas inlet tube. Heat gently on a steam bath for 4 hours; then reflux vigorously over a flame for 30 minutes while passing a rapid stream of carbon dioxide through the solution. Acidify the solution while still hot by adding 180 microL of concentrated hydrochloric acid at the bottom of the flask using a Pasteur pipette. Allow to cool to room temperature, chill in an ice bath. Subsequently add 2 ml of dichloromethane and shake gently and leave the two phases to separate. Take away the lower layer of dichloromethane. Wash the water phase with another 2 ml of dichloromethane and take the combined organic phases to dryness. Redissolve the synthesis products in 500 microL of methanol and separate the mixture of 5- and 7- carboxylic acid Statan A by HPLC separation on a Waters Prep Nova-Pak C18 cartridge (25×100 mm, 6 micro m) using $H_2O/CH_3CN$ (55:45) as mobile phase at a flow rate of 2 mL/min.

Example 11

Triflouroacetylation of Statan A in Positions 3 and 8'

Synthesis and Recovery of 3,8'-Statanyl-di-triflouracetate

Dissolve 38 mg of Statan A in 10 percent sodium hydroxide (200 microL) in a glass vial (2 ml). Add crushed ice (ca. 50 mg) and triflouracetic anhydride (50 mg) to the vial and shake it for 5 minutes. Subsequently add 200 microL of dichloromethane and shake gently and leave the two phases to separate. Take away the lower layer of dichloromethane and and shake it with dilute sodium bicarbonate. Add another 200 microL of dichloromethane to the slightly basic water phase and wash the organic phase with dilute sodium bicarbonate. Take the combined organic phases to dryness to recover 58 mg (93%) of the statan di-triflouroacetate.

Example 12

Formation of 6-Methyl-statan A—Friedel Craft

Dissolve 58 mg of 3,8'-statanyl-di-triflouracetate in methylcyclohexane (4 mL) in a small glass flask fitted with a drying tube ($CaCl_2$). Add anhydrous aluminium chloride (9 mg). Cool the flask in an ice bath and while stirring (with a small rotating magnet) add methyl chloride (11 mg) during the following 4 hours, maintaining the temperature in the cooling bath at 0–5° C. Stir the mixture for another hour after addition is complete, remove the drying tube, add crushed ice (2 g) in portions, with stirring, to decompose the intermediate addition compounds. Take away the upper organic layer and take it to dryness. Redissolve the residues in 10 percent sodium hydroxide (2 mL) in a glass vial flask and boil the solution under reflux for an hour to remove the triflouroacetate groups by hydrolysis. Cool the mixture and add dilute sulphuric acid, with stirring, until the solution is acid to litmus. Leave the solution for 30 minutes for the intramolecular lactonisation to complete. Now extract the product from the water phase into (2×500 microL) of freshly distilled diethylether. Evaporate of the diethylether and redissolve the synthesis products in 500 microL of methanol. Separate the mixture by HPLC on a Waters Prep Nova-Pak C18 cartridge (25×100 mm, 6 micro m) using a gradient of $H_2O/CH_3CN$ as mobile phase going from (70:30) to (30:70) in 15 minutes using a flow rate of 2 ml/min to give 11 mg (30%) of pure 6-methyl-statan A.

Exampel 13

Test of Cholesterol-lowering Effect of Statans in Rabbits

The cholesterol-lowering effect of Statan A was compared against a control in male White rabbits (purchased from Hvidesten, DK). The rabbits were housed in individual stainless steel cages with free access to water. The rabbits were divided into groups with similar baseline values of plasma cholesterol, which groups received:
1) 5 mg/day PD498 (n=2)(Statan A),
2) control group (n=4).

The rabbits were treated for 3 days. All animals were fed daily with 100 g of a standard rabbit diet (Altromin, Lage, Germany) containing 1% cholesterol. All test drugs were added to the diet. Remaining food were weighed.

Blood samples for cholesterol determination were drawn at baseline and at the three following days. Blood samples were taken from the marginal ear vein and the cholesterol determination was done the same day by enzymatic calorimetric methods, using a commercially available kit (CHOD-PAP, Roche), on a COBAS MIRA auto-analyzer (Roche, Basle, CH).

Figure 2:
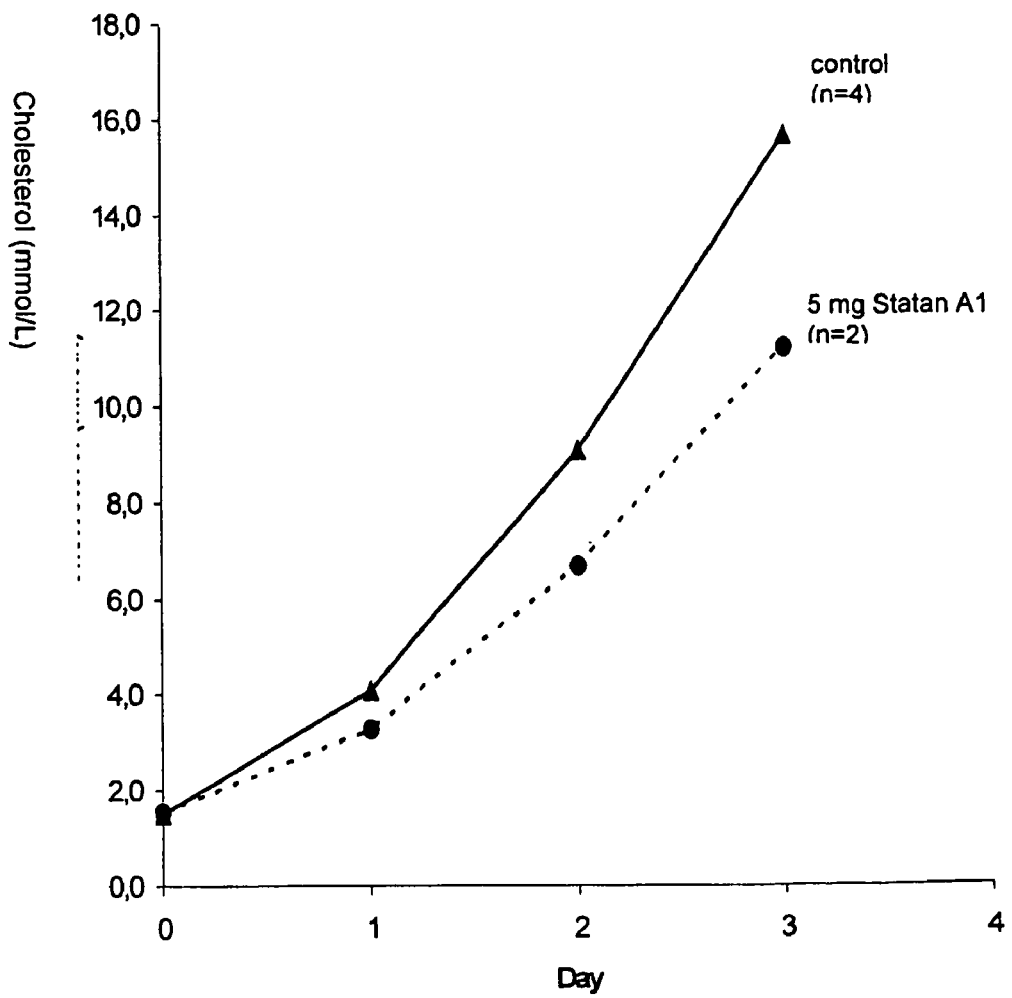
FIG. 2 shows the development in total plasma cholesteol (avarege) of Statan A in rabbits.

The results of the present study are shown in FIG. 2. Total plasma cholesterol levels in the Statan A group were consistently lower, when compared to the control group. These results show a cholesterol-lowering effect of Statan A with a strong tendency towards lower plasma cholesterol values.

Chow Preparation

Ten kg 1% cholesterol chow: 100 g cholesterol is dissolved in 500 g corn oil by heating to 40° C. The cholesterol mixture is well-mixed with 9400 g standard rabbit chow (Altromin, Hvidesten, DK).
35 3.5 kg 1% cholesterol chow with test compound is dissolved in 40 mL corn oil and ultrasonicated for 10 min and then well-mixed with 3.5 kg of the cholesterol-enriched chow.

5 mg/day of Statan A: 30 mg Statan A is dissolved in 1000 microL ethanol (100%). 30 mL corn oil is added and heated to 40° C. The mixture is well-mixed with 3.5 kg of the cholesterol-enriched chow.

As an alternative method to the above disclosed method the rabbits are selected as hyper-, normo- or hyporesponsive to dietary cholesterol. The hyposensitive rabbits are fed with 1% cholesterol chow 5 days before administration of the test drug. Thereafter the rabbits are fed daily for 3 days with the cholesterol-enriched (1%) chow containing the test drugs.

Example 14

Test of Cholesterol-lowering Effect of Solistatin in Rabbits

The cholesterol-lowering effect of solitstatin was tested in rabbits using the same method as disclosed in Example 13. The test indicated that solistatin had cholesterol-lowering effect.

The invention claimed is:

1. An isolated compound of formula (I)

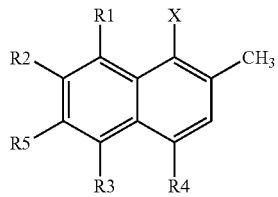

(I)

wherein
R1 is OH, $C_6H_5COO$, or R6COO wherein R6 is $C_1$–$C_5$ alkyl;
R2 is H, $C_1$–$C_5$ alkyl, or $C_1$–$C_5$ acyl;
R3 is H, $C_1$–$C_5$ alkyl, or $C_1$–$C_5$ acyl;
R4 is H, $C_1$–$C_5$ alkyl, or $C_1$–$C_5$ acyl;
R5 is H or $CH_3$; and
X is a compound of formula (II) or (III)

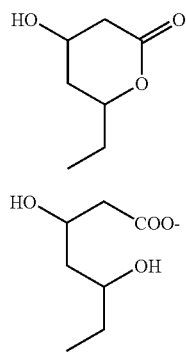

or a physiologically-hydrolyzable and pharmaceutically acceptable ester thereof or a pharmaceutically acceptable salt thereof.

2. A compound of claim 1, wherein R is 2-methylbuturyl or 2-dimethylbutyryl.

3. A compound of claim 1, wherein R2 is H.

4. A compound of claim 1, wherein R3 is H.

5. A compound of claim 1, wherein R4 is H.

6. A compound of claim 1, wherein X is a compound of formula II.

7. A compound of claim 1, wherein $R_1$ is 2-methylbutyryl or 2-dimethylbutyryl, R2 is H, R3 is H, and R4 is H.

8. A compound of claim 1, having the formula (IV)

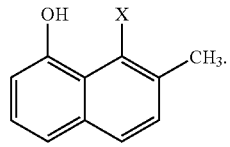

9. A pharmaceutical composition comprising:
a) at least one compound of claim 1, and
b) a pharmaceutical acceptable carrier or diluent.

10. The pharmaceutical composition of claim 9, further comprising acetylsalicylic acid.

11. A method for treating hypercholesterolemia in an mammal, comprising administering to the mammal an effective amount of at least one compound of claim 1.

12. A method of claim 11, wherein the mammal is a human.

13. A method for treating osteoporosis in an mammal, comprising administering to the mammal an effective amount of at least one compound of claim 1.

14. A method of claim 13, wherein the mammal is a human.

15. A method of reducing the level of tow-density lipoprotein cholesterol (LDL-C) in an mammal, comprising administering to the mammal an effective amount of at least one compound of claim 1.

16. A method of claim 15, wherein the mammal is a human.

17. A method of suppressing an immune response in a mammal, comprising administering to the mammal an effective amount of at least one compound of claim 1.

18. A method of claim 17, wherein the mammal is a human.

* * * * *